(12) United States Patent
Shaw

(10) Patent No.: US 6,548,541 B1
(45) Date of Patent: Apr. 15, 2003

(54) CARBOPLATIN ANALOGS FOR CANCER TREATMENT

(75) Inventor: Jiajiu Shaw, Ann Arbor, MI (US)

(73) Assignee: Unitech Pharmaceuticals, Inc., Ann Arbor, MI (US)

(*) Notice: Subject to any disclaimer, the term of this patent is extended or adjusted under 35 U.S.C. 154(b) by 0 days.

(21) Appl. No.: 09/552,167

(22) Filed: Apr. 18, 2000

Related U.S. Application Data

(60) Provisional application No. 60/130,530, filed on Apr. 21, 1999.

(51) Int. Cl.$^7$ ........................ A01N 55/02; A61K 31/28
(52) U.S. Cl. ........................ 514/492; 556/137; 556/136
(58) Field of Search ................ 514/44, 2, 492; 435/320.1; 424/180.1; 556/137, 136

(56) References Cited

U.S. PATENT DOCUMENTS

| | | | |
|---|---|---|---|
| 4,228,090 A | | 10/1980 | Hydes et al. |
| 5,178,876 A | * | 1/1993 | Khokhar et al. ............ 424/450 |
| 5,844,001 A | | 12/1998 | McClay et al. |
| 5,922,689 A | | 7/1999 | Shaw |
| 5,958,892 A | * | 9/1999 | Mukhopadhyay et al. .... 514/44 |

OTHER PUBLICATIONS

Miller, B.; Wild, S.; Zorbas, H.; Beck, W. "Synthesis and biological activity of cis–dichloro mono–and bis(platinum) complexes with N–alkyl–ethylenediamine ligands," *Inorganica Chimica Acta*, 1999, 290, pp. 237–246.

Kuebler, Jr., J. R.; Bailar, Jr., J. C. "The Stereoisomerism of Complex Inorganic Compounds, XIV, Studies upon the Stereochemistry of Saturated Tervalent Nitrogen Compounds," *J. Am. Chem. Soc.*, 1952, 74, pp. 3535–3538.

Pinkard, F. W.; Sharratt, E.; Wardlaw, W.; Cox, E. G. "Isomerides of Quadricovalent Palladium and Platinum," *J. Chem. Soc.*, 1934, pp. 1012–1016.

* cited by examiner

*Primary Examiner*—Deborah D. Carr
(74) *Attorney, Agent, or Firm*—Brinks Hofer Gilson & Lione; Gregory H. Zayia

(57) ABSTRACT

The synthesis and the use of a series of carboplatin analogs is disclosed. These carboplatin analogs may be represented by cis-Pt(II)$L^1L^2$, wherein each of $L^1$ and $L^2$, independently, is the carboxylate of phosphatidylserine, an α-amino acid, a β-amino acid, or a derivative thereof, wherein each ligand is bidentate with —$NH_2$ and —$COO^-$ as the binding sites. The complexes can be used in the treatment of cancer.

18 Claims, No Drawings

CARBOPLATIN ANALOGS FOR CANCER TREATMENT

This application claims priority under 35 U.S.C. § 119(e) to U.S. Provisional Patent Application Serial No. 60/130,530 filed Apr. 21, 1999.

BACKGROUND OF THE INVENTION

This invention relates to the synthesis of a series of carboplatin analogs which can be reversibly activated and deactivated and the use of these carboplatin analogs to treat cancer.

Cisplatin (cis-diaminedichloroplatinum, cis-Pt(NH$_3$)$_2$Cl$_2$) was the first anticancer platinum drug. It has been used as a chemotherapeutic agent for many years since the discovery of its anti-tumor activity by B. Rosenberg et. al. (*Nature*, 1965, 205: 698; *Nature*, 1972, 222: 385).

Chemical & Engineering News (Oct. 23, 1995) reported that "Cisplatin was first synthesized in the 1800s, but its anticancer activity was not discovered until the 1960s. In 1979, it was approved by the Food and Drug Administration for clinical treatment of testicular and ovarian tumors and cancers of the head and neck. Cisplatin and an analog, carboplatin, are now among the most widely used anticancer drugs."

The Physician's Desk Reference (PDR) reports that cisplatin (the commercial name is Platinol®) can be used to treat testicular cancer, ovarian cancer, and bladder cancer. Rosenberg et al., U.S. Pat. No. 4,177,263, describes methods of treating cancer using cisplatin and cisplatin analogs. The compound was shown to be effective for treating leukemia and tumors induced in mice.

After so many years, cisplatin is still being widely used because of its efficacy. However, its critical drawback, the toxicity, is still a major concern.

Many people have attempted to change the ligand on platinum to make cisplatin analogs in order to reduce the toxicity or improve the efficacy. Examples are made by K. C. Tsou, et al. (*J Clin. Hemat. Oncol.*, 7: 322 (1977)); R. J. Speeder et al. (*J Clin. Hemat. Oncol*, 7: 210 (1977)); A. Mathew et al. (*Chem. Comm.*, 222 (1979)); D. Rose, et al. (*Cancer Treatment Reviews*, 12: 1 (1985)); and D. Alberts et al. (*Cancer Treatment Reviews*, 12, 83 (1985)).

In recent years, another platinum drug, carboplatin (Paraplatin®), has been widely prescribed. As a cisplatin analog, carboplatin is becoming more popular than cisplatin because it has a better therapeutic index. In other words, carboplatin has a better efficacy/toxicity ratio when used in the treatment of cancer. Nevertheless, carboplatin still has significant side effects and it has been used to treat only certain cancers. Therefore, there is a need to further improve carboplatin to make it less toxic or more versatile.

BRIEF SUMMARY OF THE INVENTION

This invention comprises the synthesis of a series of platinum(II) complexes as carboplatin analogs for the treatment of cancer. These platinum(II) complexes can be reversibly activated/deactivated in media with different pH values. These platinum(II) complexes can have a significantly reduced drug resistance. Because the ligands are abundant biologically, the drug resistance can be less than that of cisplatin or carboplatin. In addition, they can be used in treating cancers that are not treated by cisplatin or carboplatin because of the variety of the ligands.

Other objects, features, and advantages of the present invention will become apparent from the following detailed description. It should be understood that the detailed description and the specific examples, while indicating preferred embodiments of the invention, are given by way of illustration only, since various changes and modifications within the spirit and scope of the invention will become apparent to those skilled in the art from this detailed description.

DETAILED DESCRIPTION OF THE INVENTION

One aspect of this invention is to significantly improve the performance of platinum drugs. Thus, a series of platinum (II) complexes are presented herein as carboplatin analogs. The platinum(II) complexes of this invention are similar to carboplatin in that each complex has two active sites individually protected by carboxylate groups. However, because each carboxylate group is part of the respective bidentate ligand, hydrolysis of the carboxylate only separates it from the Pt(II) ion, but not the molecule. Therefore, both carboxylate groups are able to reattach to Pt(II) under a higher pH condition, such as the normal biological condition. This behavior makes the complexes significantly different from carboplatin, in which carboxylate groups, when hydrolyzed, are permanently separated from the Pt(II) ion. As a result, these platinum(II) complexes can be much less toxic than other platinum drugs.

Another aspect of the present invention is to reduce the drug resistance after repeated treatment that is often seen with cisplatin or carboplatin treatment. Unlike carboplatin, the platinum(II) complexes of this invention utilize the carboxylate of phosphatidylserine, α-amino acids, β-amino acids, or their derivatives as the ligands. Because the platinum(II) is camouflaged by these ligands, which are abundant in living organisms, these complexes are much less likely to incur drug resistance on repeated treatment. Therefore, the carboplatin analogs of this invention have advantages over cisplatin or carboplatin.

Yet another aspect of the present invention is to expand the number and the types of cancer in which the complexes can be effectively used. Cisplatin and carboplatin have been used only in some cancers, such as testicular and ovarian tumors, cancers of the head and neck, etc. It would be greatly beneficial to expand the use of platinum drugs to treat cancers that are not being treated by cisplatin and carboplatin.

The platinum(II) complexes of the present invention can have significantly different physical properties (such as solubility, affinity, permeability, stereo effect, etc.) from those of cisplatin or carboplatin because of the variety of ligands that can be used and because of the ability of amino acids to induce and stabilize some limited conformation themselves or when incorporated into small peptides. Therefore, these complexes can be useful in treating cancers that are not treated by cisplatin or carboplatin.

Therefore, the platinum(II) complexes of this invention have several distinct advantages over carboplatin including (1) they can be reversibly activated and deactivated, (2) they can have a significantly reduced drug resistance, and (3) they can be used to treat cancers that are not treated by cisplatin or carboplatin.

Platinum(II) Complexes Of The Present Invention

The complexes of the present invention can be represented by cis-Pt(II)L$^1$L$^2$, wherein each of L$^1$ and L$^2$, independently is the carboxylate of phosphatidylserine, an α-amino acid, a β-amino acid, or a derivative thereof, wherein each ligand is bidentate with –NH$_2$ and –COO$^-$ as the binding sites.

The following structure represents cis-Pt(valine)$_2$:

(STRUCTURE 1)

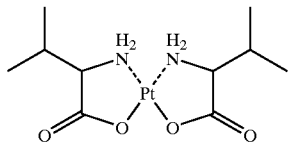

Suitable acid, such as HCl, HBr, or HNO$_3$, can be added to the complexes to make the free acid form, cis-Pt(II)Cl$_2$L$^1$L$^2$, cis-Pt(II)Br$_2$L$^1$L$^2$ or cis-Pt(II)(NO$_3$)$_2$L$^1$L$^2$ wherein each ligand is monodentate with –NH$_2$ as the binding site. The structure of PtCl$_2$(Valine)$_2$ is shown as an example:

(STRUCTURE 2)

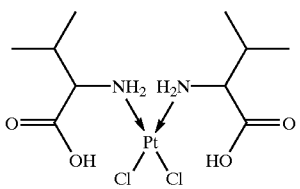

The α- amino acid, β-amino acid, or derivative thereof, includes but is not limited to, alanine, aspartic acid, glutamic acid, glycine, isoleucine, leucine, phenylalanine, proline, serine, threonine, tyrosine, and valine.

Similar to carboplatin, the platinum(II) complexes of the present invention are more likely to be hydrolyzed in a cancerous area where the pH is lower than the normal biological pH. Thus, the two platinum(II) active sites are exposed to interact with DNA. In contrast to carboplatin, the active sites of the platinum(II) complex in this invention can be re-protected when they enter into a non-cancerous area because of the higher pH value. The activation/deactivation process for the platinum(II) complex is reversible. Therefore, potential side effects can be significantly reduced.

The reversible activation/deactivation reaction of the complexes of this invention may be illustrated by the example below:

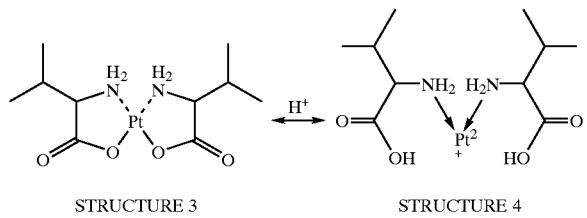

STRUCTURE 3          STRUCTURE 4

Whereas for carboplatin, it is a one-way reaction as illustrated below:

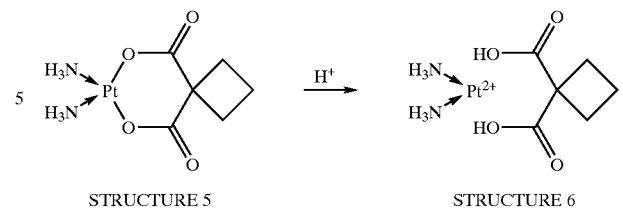

STRUCTURE 5          STRUCTURE 6

Therefore, these platinum(II) complexes or their free acids can be used in treating cancer, and the platinum(II) complexes of the present invention are expected to have better therapeutic indices than carboplatin and cisplatin.

Another advantage of these platinum(II) complexes is that the platinum(II) ion is camouflaged by amino acids, which are abundant in living organisms. This fact makes it much less likely to incur drug resistance. Drug resistance for anticancer drugs (such as cisplatin and carboplatin) is well known for repeated treatment.

Yet another advantage of these platinum(II) complexes is that they can be used to treat those cancers that are not treated by cisplatin or carboplatin. This is because of the variety of ligands on these complexes, which covers a wide range of physical/chemical properties, such as solubility, permeability, ionic charge, etc. Therefore, some of these complexes can be used to treat certain cancers while others can be used to treat other cancers. In other words, these complexes can be used to treat a much broader range of various types of cancers.

Pharmaceuticals and Methods of Treating Cancer

In one aspect, the present invention provides methods for the treatment of various malignancies. Treatment methods involve treating an individual with an effective amount of the platinum(II) complexes of this invention, as described herein. An effective amount is defined, generally, as that amount sufficient to detectably and repeatedly ameliorate, reduce, minimize, or limit the extent of a disease or its symptoms. More rigorous definitions may apply, including elimination, eradication or cure of disease.

To kill cells, inhibit cell growth, inhibit metastasis, decrease tumor size, and otherwise reverse or reduce the malignant phenotype of tumor cells, using the methods and compositions of the present invention, one would generally contact a "target" cell with the platinum(II) complexes of this invention. This may be combined with compositions comprising other agents effective in the treatment of cancer. These compositions would be provided in a combined amount effective to kill or inhibit proliferation of the cells. This process may involve contacting the cells with platinum (II) complexes of this invention and the agent(s) or factor(s) at the same time. This may be achieved by contacting the cells with a single composition or pharmacological formulation that includes both agents, or by contacting the cells with two distinct compositions or formulations at the same time, wherein one composition includes one or more platinum(II) complex of this invention and the other includes the second agent.

Alternatively, the therapy with the platinum(II) complexes of this invention can precede or follow treatment with the other agent by intervals ranging from minutes to weeks. In embodiments where the other agent and the platinum(II) complexes of this invention are applied separately to the cells, one would generally ensure that a significant period of time did not expire between the time of each delivery, such that the agent and the platinum(II) complexes of this invention would still be able to exert an advantageously combined effect on the cell. In such instances, one would contact the cells with both modalities within about 12–24 hours of each other and, more preferably, within about 6–12 hours of each other, with a delay time of only about 12 hours being most preferred. In some situations, it may be desirable to extend the time period for treatment significantly, however, where several days (2, 3, 4, 5, 6, or 7 days) to several weeks (1, 2, 3, 4, 5, 6, 7, or 8 weeks) lapse between the respective administrations.

Administration of the therapeutic platinum(II) complexes of the present invention to a patient follow general protocols for the administration of chemotherapeutics, taking into account the toxicity, if any, of the platinum(II) complexes. Treatment cycles can be repeated as necessary. Various standard therapies, as well as surgical intervention, can be applied in combination with the described therapy.

Where clinical application of a particular therapy is contemplated, it is necessary to prepare the complex as a pharmaceutical composition appropriate for the intended application. Generally this entails preparing a pharmaceutical composition that is essentially free of pyrogens, as well as any other impurities that could be harmful to humans or animals. It is also generally desirable to employ appropriate salts and buffers to render the complex stable and allow for complex uptake by target cells.

Aqueous compositions of the present invention comprise an effective amount of the compound, dissolved or dispersed in a pharmaceutically acceptable carrier or aqueous medium. Such compositions can also be referred to as inocula. The phrases "pharmaceutically or pharmacologically acceptable" refer to molecular entities and compositions that do not produce an adverse, allergic or other untoward reaction when administered to an animal, or a human, as appropriate. As used herein, "pharmaceutically acceptable carrier" includes any and all solvents, dispersion media, coatings, antibacterial and antifungal agents, isotonic and absorption delaying agents, and the like. The use of such media and agents for pharmaceutical active substances is well known in the art. Except insofar as any conventional media or agent is incompatible with the active ingredient, its use in the therapeutic compositions is contemplated. Supplementary active ingredients also can be incorporated into the compositions.

The compositions of the present invention may include classic pharmaceutical preparations. Dispersions also can be prepared in glycerol, liquid polyethylene glycols, and mixtures thereof, and in oils. Under ordinary conditions of storage and use, these preparations contain a preservative to prevent the growth of microorganisms.

Depending on the particular cancer to be treated, administration of therapeutic compositions according to the present invention can be via any common route as long as the target tissue is available via that route. This includes oral, nasal, buccal, rectal, vaginal or topical. Topical administration would be particularly advantageous for treatment of skin cancers. Alternatively, administration can be by orthotopic, intradermal, subcutaneous, intramuscular, intraperitoneal or intravenous injection. Such compositions can normally be administered as pharmaceutically acceptable compositions that include physiologically acceptable carriers, buffers, or other excipients.

The treatments can include various "unit doses." Unit dose is defined as containing a predetermined quantity of the therapeutic composition calculated to produce the desired responses in association with its administration, i.e., the appropriate route and treatment regimen. The quantity to be administered, and the particular route and formulation, are within the skill of those in the clinical arts. Also of import is the subject to be treated, in particular, the state of the subject and the protection desired. A unit dose need not be administered as a single injection or administration, but may comprise continuous infusion over a set period of time.

Preferably, patients have adequate bone marrow function (defined as a peripheral absolute granulocyte count of >2,000/mm$^3$ and a platelet count of 100,000/mm$^3$), adequate liver function (bilirubin <1.5 mg/dl), and adequate renal function (creatinine <1.5 mg/dl).

One of the preferred embodiments of the present invention involves the use of the platinum(II) complexes of this invention to treat cancer cells. Target cancer cells include, but are not limited to, cancers of the lung, brain, prostate, kidney, liver, ovary, endometrium, breast, skin, stomach, esophagus, head and neck, testicles, germ cancer, epithelial, colon, small intestine, thyroid, cervix, pancreas, glioblastoma, astrocytoma, oligodendroglioma, ependymomas, neurofibrosarcoma, meningia, lymphatic system, and blood. Of particular interest are non-small cell lung carcinomas including squamous cell carcinomas, adenocarcinomas, and large cell undifferentiated carcinomas.

According to the present invention, one can treat the cancer by directly injecting a tumor with the therapeutic compositions of the present invention. Alternatively, the tumor can be infused or perfused with the therapeutic composition using any suitable delivery vehicle. Local or regional administration, with respect to the tumor, is also contemplated. Finally, systemic administration can be performed. In certain embodiments, the contacting comprises delivering the therapeutic composition endoscopically, intratracheally, intralesionally, percutaneously, intravenously, subcutaneously, or intratumorally to the subject.

Continuous administration can also be applied where appropriate, for example, where a tumor is excised and the tumor bed is treated to eliminate residual, microscopic disease. Delivery via syringe or catherization is also contemplated. Such continuous perfusion can take place for a period from about 1–2 hours, about 2–6 hours, about 6–12 hours, about 12–24 hours, about 1–2 days, about 1–2 weeks or longer, following the initiation of treatment. Generally, the dose of the therapeutic composition via continuous perfusion is equivalent to that given by a single or multiple injections, adjusted over a period of time during which the perfusion occurs.

For tumors of >4 cm, the volume to be administered is be about 4–10 mL (preferably about 10 mL), while for tumors of <4 cm, a volume of about 1–3 mL is used (preferably about 3 mL). Multiple injections delivered as single dose comprise about 0.1 to about 0.5 mL volumes. The tumor may advantageously be contacted by administering the therapeutic composition in multiple injections to the tumor, spaced at approximately 1 cm intervals.

In certain embodiments, the tumor being treated may not, at least initially, be resectable. Treatments with therapeutic composition may increase the resectability of the tumor due to shrinkage at the margins or by elimination of certain particularly invasive portions. Following treatments, resection may be possible. Additional treatments subsequent to resection will serve to eliminate microscopic residual disease at the tumor site. In certain embodiments, tumor resection may occur prior to the contacting. The tumor resection may be performed one, two, three or more times.

A typical course of treatment, for a primary tumor or a post-excision tumor bed, involves multiple doses. Typical primary tumor treatment involves a 6-dose application over a two-week period. The two-week regimen may be repeated one, two, three, four, five, six or more times. During a course of treatment, the need to complete the planned dosings may be re-evaluated.

Cancer therapies also include a variety of combination therapies with both chemical and radiation based treatments. Combination chemotherapies include, for example, cisplatin, procarbazine, mechlorethamine, cyclophosphamide, camptothecin, ifosfamide, melphalan, chlorambucil, bisulfan, nitrosurea, dactinomycin, daunorubicin, doxorubicin, bleomycin, plicomycin, mitomycin, etoposide (VP16), tamoxifen, taxol, transplatinum, 5-fluorouracil, vincristin, vinblastin, and methotrexate, or any analog or derivative variant thereof.

Other factors that cause DNA damage and have been used extensively include what are commonly known as γ-rays, X-rays, and/or the directed delivery of radioisotopes to tumor cells. Other forms of DNA damaging factors are also contemplated such as microwaves and UV-irradiation. It is most likely that all of these factors effect a broad range of damage on DNA, on the precursors of DNA, on the replication and repair of DNA, and on the assembly and maintenance of chromosomes. Dosage ranges for X-rays range from daily doses of 50 to 200 roentgens for prolonged periods of time (3 to 4 weeks), to single doses of 2000 to 6000 roentgens. Dosage ranges for radioisotopes vary widely, and depend on the half-life of the isotope, the strength and type of radiation emitted, and the uptake by the neoplastic cells.

In addition, gene therapy is becoming increasingly useful for treating cancers. In such embodiments, expression constructs comprising viral vectors containing the therapeutic genes are used to in order to induce an apoptotic effect in cancer cells. The viral vectors may be adenoviral (see for example, U.S. Pat. No. 5,824,544; U.S. Pat. No. 5,707,618; U.S. Pat. No. 5,693,509; U.S. Patent No. 5,670,488; U.S. Pat. No. 5,585,362, each incorporated herein by reference), retroviral (see for example, U.S. Pat. No. 5,888,502; U.S. Pat. No. 5,830,725; U.S. Pat. No. 5,770,414; U.S. Pat. No. 5,686,278; U.S. Pat. No. 4,861,719, each incorporated herein by reference), an adeno-associated viral (see for example, U.S. Pat. No. 5,474,935; U.S. Pat. No. 5,139,941; U.S. Pat. No. 5,622,856; U.S. Pat. No. 5,658,776; U.S. Pat. No. 5,773,289; U.S. Pat. No. 5,789,390; U.S. Pat. No. 5,834,441; U.S. Pat. No. 5,863,541; U.S. Pat. No. 5,851,521; U.S. Pat. No. 5,252,479, each incorporated herein by reference), an adenoviral-adenoassociated viral hybrid (see for example, U.S. Pat. No. 5,856,152, incorporated herein by reference) a vaccinia viral or a herpesviral (see for example, U.S. Pat. No. 5,879,934; U.S. Pat. No. 5,849,571; U.S. Pat. No. 5,830,727; U.S. Pat. No. 5,661,033; U.S. Pat. No. 5,328,688, each incorporated herein by reference) vector. These vectors are contacted with the cancer cells to produce the therapeutic effect. The viral expression construct comprising a nucleic acid encoding a therapeutic anticancer gene can contain any cancer therapy gene known to those of skill in the art including, but not limited to, p53, p16, p21, MMAC1, p73, zaci, C-CAM, BRCAI, Rb, Bax, Bak, Bim, Bik, Bid, Bad gene, Harakiri, Ad EIB, an ICE-CED3 protease, a cytokine such as IL-2, IL-2, IL-3, IL-4, IL-5, IL-6, IL-7, IL-8, IL-9, IL- 10, IL-11, IL-12, IL-13, IL-14, IL-15, TNF, GMCSF, β-interferon, and γ-interferon. In other embodiments, the therapeutic nucleic acid may be an antisense nucleic acid directed against an oncogene.

It is understood that the expression vectors comprising the therapeutic genes to be used in combination with the compositions of the present invention will further comprise the appropriate promoters, enhancers, and other regulator elements necessary for efficient replication to occur. Such elements are well known to those of skill in the art. Exemplary promoters for use herein include, but are not limited to, CMV IE, SV40 IE, RSV, β-actin, tetracycline regulatable, and ecdysone regulatable. By "treatment," the present invention refers to any event that decreases the growth, kills, or otherwise abrogates the presence of cancer cells in a subject. Such a treatment can also occur by inhibition of the metastatic potential or inhibition of tumorigenicity of the cells so as to achieve a therapeutic outcome.

Various combinations can be employed. For example, where the platinum(II) complexes of the present invention are represented by "A" and the gene, radiotherapeutic, or chemotherapeutic agent is represented by "B", combinations can include:

| | | | | | |
|---|---|---|---|---|---|
| A/B/A | B/A/B | B/B/A | A/A/B | A/B/B | B/A/A |
| A/B/B/B | B/A/B/B | B/B/B/A | B/B/A/B | A/A/B/B | A/B/A/B |
| A/B/B/A | B/B/A/A | B/A/B/A | B/A/A/B | A/A/A/B | B/A/A/A |
| A/B/A/A | A/A/B/A | | | | |

The terms "contacted" and "exposed," when applied to a cell, are used herein to describe the process by which a platinum(II) complex of this invention and a gene therapeutic construct, a chemotherapeutic, or radiotherapeutic agent are delivered to a target cell or are placed in direct juxtaposition with the target cell. To achieve cell killing or stasis, both agents are delivered to a cell in a combined amount effective to kill the cell or prevent it from dividing.

The therapeutic compositions of the present invention are advantageously administered in the form of injectable compositions either as liquid solutions or suspensions, solid forms suitable for solution in, or suspension in, liquid prior to injection can also be prepared. These preparations also may be emulsified. A typical composition for such purpose comprises a pharmaceutically acceptable carrier. For instance, the composition may contain 10 mg, 25 mg, 50 mg or up to about 100 mg of human serum albumin per milliliter of phosphate buffered saline. Other pharmaceutically acceptable carriers include aqueous solutions, non-toxic excipients, including salts, preservatives, buffers, and the like. Examples of non-aqueous solvents are propylene glycol, polyethylene glycol, vegetable oil, and injectable organic esters such as ethyloleate. Aqueous carriers include water, alcoholic/aqueous solutions, saline solutions, parenteral vehicles such as sodium chloride, Ringer's dextrose, etc. Intravenous vehicles include fluid and nutrient replenishers. Preservatives include antimicrobial agents, anti-oxidants, chelating agents, and inert gases. The pH and exact concentration of the various components in the pharmaceutical composition are adjusted according to well known parameters.

Additional formulations are suitable for oral administration. Oral formulations include such typical excipients as, for example, pharmaceutical grades of mannitol, lactose, starch, magnesium stearate, sodium saccharine, cellulose, magnesium carbonate, and the like. The compositions take the form of solutions, suspensions, tablets, pills, capsules, sustained release formulations, or powders. When the route is topical, the form can be a cream, ointment, salve. or spray.

EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Synthesis of the Pt(L-Tyrosine)$_2$ by a heterogeneous method.

Weigh 83 mg (0.2 mmole) of $K_2PtCl_4$ and dissolve it in 100 mL deionized water. Weigh 72 mg (0.4 mmole) of L-tyrosine and add it to the $K_2PtCl_4$ solution. (Note: L-tyrosine is almost insoluble in water.) Adjust the pH to ca. 8 with sodium hydroxide or sodium bicarbonate. Mix the aliquot at about 35° C. for 2–4 days. The aliquot gradually becomes a solution and the color changes from very light tea color to light brown. The UV spectrum shows an additional maximum at about 320 nm. Concentrate the solution under vacuum. Use a suitable solvent system to re-crystallize the product by standard technique.

Example 2

Synthesis of Pt(L-alanine)$_2$ by a homogeneous method.

Weigh 83 mg (0.2 mmole) of $K_2PtCl_4$ and dissolve it in 100 mL deionized water. Weigh 35.6 mg (0.4 mmole) of L-alanine and dissolve it in the $K_2PtCl4$ solution. Adjust the pH to ca. 8 with sodium hydroxide or sodium bicarbonate. Mix the aliquot for 2–4 days at room temperature. The solution gradually changes color from light brown to brown. Concentrate the solution under vacuum. Use a suitable solvent system to re-crystallize the product by standard technique.

Example 3

Synthesis of Pt(L-alanine)(L-tyrosine).

Make Pt(L-alanine)Cl$_2$ according to Example 2 except only half of the L-alanine is required. Add the same number of moles for Pt(L-alanine)Cl$_2$ and L-tyrosine in a suitable amount of water, adjust the pH to ca. 8, and mix it for 2–4 days at room temperature. Proceed as in the previous example to purify the product.

Example 4

Synthesis of Pt(L-alanine)(phosphatidylserine).

The same method as in Example 3 is used to synthesize Pt(L-alanine) (phosphatidylserine).

Example 5

The in-vitro effects of sample #01 1700 on human squamous carcinoma clone cancer cell line (SCC-1).

Sample #01 1700 is $PtCl_2[CH_3CH(NH)_2COOH]_2$ where $CH_3CH(NH)_2COOH$ is alanine.

All cell culture plasticware was purchased from Fisher. Media and antibiotics were purchased from Gibco and Sigma.

Cell viability using a Coulter Counter is used to quantify toxicity. SCC-1 cells are grown in MEM media containing 10% Fetal Bovine Serum, 100 units/ml penicillin, 100 1$\mu$/ml streptomycin, and 2.5 $\mu$g/ml fungizone at 37° C. in a 5% $CO_2$ incubator. A 6 well dish is inoculated to $2.0 \times 10^5$ cells/well in a total volume of media of 2 ml. Incubation occurs overnight and the cells are ready for treatment the next day.

Stock solution of sample #01 1700 is sterile filtered with a 0.22 $\mu$m low protein binding syringe filter. Dilutions are made in fresh MEM-10% FBS.

Two days after treatment at 37° C., cells are harvested and quantified using a Coulter Counter. To harvest, all media is removed and 1 ml of 1× trypsin solution is added per well. Tryspin is in the well for approximately 5 minutes at 37° C. After 5 minutes, 1 ml of fresh MEM-10% FBS is added per well. Upon vigorous mixing to ensure breakup of aggregate cells, dilutions are made in Isoton®II ready for cell counts. Each well is counted twice. Thus, duplicate wells plus duplicate counts yield 4 cell counts per parameter above.

The results shown in the following table indicate that #01 1700 shows inhibition of the growth of SCC-1 cells in-vitro.

| $\mu$M #011700 | Cell Count/mL |
| --- | --- |
| 0 | $5.70 \times 10^5$ |
| 20 | $6.00 \times 10^5$ |
| 30 | $5.80 \times 10^5$ |
| 40 | $5.20 \times 10^5$ |
| 50 | $4.40 \times 10^5$ |
| 60 | $3.80 \times 10^5$ |

The platinum(II) complexes of this invention may be formulated with customary pharmaceutical excipients to make suitable dosage forms by standard pharmaceutical techniques and processes. Such excipients include, but are not limited to, starch, cellulose, lactose, magnesium stearate, stearic acid, talc, calcium phosphate, inorganic buffer, organic buffer, surfactant, silicon dioxide, and food color. Two examples of the dosage forms are as follows:

Example 6

An example of making an injectable dosage form.

Weigh 50 mg of Pt(L-Tyrosine)$_2$ and dissolve it in 1000 mL of deionized water. A suitable amount of phosphate buffer is added to a bring the pH to about 7.4. The solution is sterilized to make an injectable dosage form.

Example 7

An example of making an oral dosage form.

A pharmaceutical dosage form for oral administration can be made from the following formulation using standard pharmaceutical techniques and equipment.

100 mg of Pt(L-alanine)(L-tyrosine)
145 mg of lactose
75 mg microcrystalline cellulose
5 mg magnesium stearate

Example 8

An example of administration of a platinum complex of this invention.

A therapeutically effective amount of a platinum(II) complex of this invention is administered to a cancer patient in a suitable dosage form.

In a therapeutic regiment, 10 mg–1000 mg of the platinum (II) complex is administered to a cancer patient by injection once every 1 to 4 weeks. The regimen can be repeated.

Example 9

An alternate example of administration of a platinum complex of this invention.

In a therapeutic regiment, 10 mg–1000 mg of a platinum (II) complex of the present invention is administered to a cancer patient orally once every 1 to 4 weeks. The regimen can be repeated.

The complexes of the present invention can also be used in the treatment of AIDS (Acquired Immune Deficiency Syndrome). Because these complexes can hamper the DNA or RNA replication process, they can be effective against the HIV (Human Immunodeficiency Virus) and may be used for the treatment of AIDS.

In conclusion, a series of platinum(II) complexes, as carboplatin analogs, are disclosed in this invention. The complexes can be represented by cis-Pt(II)$L^1L^2$, wherein each of $L^1$ and $L^2$, independently is the carboxylate of phosphatidylserine, an α-amino acid, a β-amino acid, or a derivative thereof, and wherein each ligand is bidentate with $-NH_2$ and $-COO^-$ as the binding sites. The free acids of these complexes are also disclosed. The synthesis and the use of these platinum(II) complexes are presented in this invention.

Although the description above contains many specifics, these should not be construed as limiting the scope of the invention, but as merely providing illustrations of some of the presently preferred embodiments of this invention. For example, the compounds can be made in pure water instead of the mixture of methanol and water.

Thus the scope of this invention should be determined by the appended claims and their legal equivalents, rather than by the examples given.

I claim:

1. A method of treating cancer comprising administering to a cancer patient a therapeutically effective amount of a complex with the formula cis-Pt(II)$L^1L^2$, wherein each of $L^1$ and $L^2$, independently, is the carboxylate of phosphatidylserine, an α-amino acid, a β-amino acid, the derivative of an α-amino acid, or the derivative of a β-amino acid, wherein each ligand is bidentate with $-NH_2$ and $—COO^-$ as binding sites.

2. The method of claim 1 wherein said cancer is breast cancer, prostate cancer, lung cancer, colon cancer, or skin cancer.

3. A pharmaceutical composition comprising:
 a) a pharmaceutically acceptable dosage form of a complex with the formula cis-Pt(II)$L^1L^2$, wherein each of $L^1$ and $L^2$, independently, is the carboxylate of phosphatidylserine, an α-amino acid, a β-amino acid, the derivative of an α-amino acid, or the derivative of a β-amino acid, wherein each ligand is bidentate with $—NH_2$ and $—COO^-$ as binding sites; and
 b) a pharmaceutically acceptable buffer, solvent, or diluent.

4. A method of treating cancer comprising administration of a therapeutically effective amount of a pharmaceutical composition of claim 3 to a cancer patient.

5. The method of claim 4 wherein said cancer is breast cancer, prostate cancer, lung cancer, colon cancer, or skin cancer.

6. The method of claim 4 wherein said pharmaceutical composition comprises about 10 mg to about 1000 mg of said complex.

7. The method of claim 4 wherein said pharmaceutical composition is administered once every one to four weeks.

8. The method of claim 7 wherein the administration of said pharmaceutical composition is repeated until remission of said cancer is observed.

9. The method of claim 4 wherein the administration of said pharmaceutical composition is oral.

10. The method of claim 4 wherein the administration of said pharmaceutical composition is parenteral.

11. The method claim 4 further comprising administration of an additional cancer therapeutic agent to a cancer patient.

12. The method of claim 11 wherein said additional cancer therapeutic agent is selected from the group consisting of irradiation, a chemotherapeutic agent, and an expression construct comprising a nucleic acid encoding a cancer therapeutic gene and a promoter operative in eukaryotic cells, wherein said nucleic acid is operatively linked to said promoter.

13. The method of claim 11, wherein said additional cancer therapeutic agent is a DNA damaging agent selected from the group consisting of verapamil, podophyllotoxin, procarbazine, mechlorethamine, cyclophosphamide, camptothecin, ifosfamide, melphalan, chlorambucil, bisulfan, nitrosurea, dactinomycin, daunorubicin, doxorubicin, bleomycin, plicomycin, mitomycin, etoposide (VP16), tamoxifen, taxol, transplatinum, 5-fluorouracil, vincristin, vinblastin, and methotrexate.

14. The method of claim 12, wherein said irradiation is selected from the group consisting of X-ray radiation, UV-radiation, γ-radiation, and microwave radiation.

15. The method of claim 12, wherein said expression construct is selected from the group consisting of an adenovirus, an adeno-associated virus, a vaccinia virus, and a herpes virus.

16. The method of claim 12, wherein said nucleic acid encodes a therapeutic gene selected from the group consisting of p53, p16, p21, MMAC1, p73, zac1, C-CAM, BRCAI, Rb, Bax, Bak, Bim, Bik, Bid, Bad gene Harakiri, Ad E1B, an ICE-CED3 protease, and a cytokine.

17. The method of claim 4, wherein said administration comprises delivering said pharmaceutical composition endoscopically, intratracheally, intralesionally, percutaneously, intravenously, subcutaneously or intratumorally.

18. The method of claim 4, wherein said administration is effected by direct injection of a tumor in said cancer patient with said pharmaceutical composition.

* * * * *